US006861218B2

(12) United States Patent
Haas et al.

(10) Patent No.: US 6,861,218 B2
(45) Date of Patent: Mar. 1, 2005

(54) METHOD FOR THE TARGETED APPLICATION OF REAGENTS ONTO IMMOBILIZED BIOLOGICAL MATERIAL

(75) Inventors: Oskar A. Haas, Kloster Neuburg (AT); Thomas Lörch, Reilingen (DE); Andreas Plesch, Schwetzingen (DE)

(73) Assignee: MetaSystems Hard and Software GmbH, Altlussheim (DE)

( * ) Notice: Subject to any disclaimer, the term of this patent is extended or adjusted under 35 U.S.C. 154(b) by 438 days.

(21) Appl. No.: 09/899,304

(22) Filed: Jul. 5, 2001

(65) Prior Publication Data

US 2002/0019003 A1 Feb. 14, 2002

Related U.S. Application Data

(63) Continuation-in-part of application No. 09/432,671, filed on Nov. 2, 1999, now abandoned.

(30) Foreign Application Priority Data

Nov. 3, 1998 (DE) ......................................... 198 50 659

(51) Int. Cl.[7] .......................... C12Q 1/68; G01N 33/53; C12P 19/34; C07H 21/02
(52) U.S. Cl. ......................... 435/6; 435/7.1; 435/91.1; 536/23.1; 530/300; 530/350
(58) Field of Search .......................... 435/6, 91.1, 183, 435/7.1; 436/177, 174; 422/94, 101; 536/23.1, 24.3, 24.33, 25.3; 530/300, 350

(56) References Cited

U.S. PATENT DOCUMENTS 5,976,970 A    11/1999  Pinkel et al.
6,358,749 B1 *  3/2002  Orthman ..................... 436/177

FOREIGN PATENT DOCUMENTS

DE          4344726 A1    6/1995
EP          0834575 A2    4/1998
WO          WO95/12808    5/1995
WO          WO97/26539    7/1997

OTHER PUBLICATIONS

Stratagene Cloning Systems, Catalog p. 121, cover & back page, 1994, California US.
Kallionierni et al, "Optimizing Comparative Genomic Hybridization for Analysis of DNA Sequence Copy Number Changes in Solid Tumors", Genes, Chromosomes & Cancer, 10:231–243, 1994, US.
The Fisher Catalog, cover, pp. 1212, 1213, 1224 & 1225, undated, Pittsburgh, PA, US.
Huber, R. et al, Automated metaphase finding: an assessment of the efficiency of the METAFER2 system in a routine mutagenicity assay, *Mutation Research Environmental*, 334 (1995) 97–102, Amersterdam (The Netherlands).
Weber, J. et al, Time–saving in biological dosimetry by using the automatic metaphase finder Metafer2, *Mutation Research*, 272(1992) 31–34, Amersterdam (The Netherlands).
d'Amore et al, Molecular Studies on Single Cells Harvested by Micromanipulation from Archival Tissue Sections Previously Stained by Immunohistochemistry or Nonisotopic In Situ Hybridization, Laboratory Investigation, vol. 76, No. 2, pp 219–224, Feb., 1997 US.
Mehes et al, "Quantitative Analysis of Disseminated Tumor Cells in the Bone Marrow by Automated Fluorescence Image Analysis" Cytometry 42:357–362, 2000, US.
Mehes et al, "Automatic Detection and Genetic Profiling of Disseminated Neuroblastoma Cells". Medical and Pediatric Oncology 36:205–209, 2001, US.

* cited by examiner

*Primary Examiner*—Kenneth R. Horlick
*Assistant Examiner*—Frank Lu
(74) *Attorney, Agent, or Firm*—J. Bennett Mullinax, LLC

(57) ABSTRACT

The present invention is relative to a method for the purposeful application of at least one reagent onto immobilized biological material as well as to a diagnostic kit containing small-area, local covers on which at least one reagent is fixed for contact hybridization.

34 Claims, 2 Drawing Sheets

METHOD FOR THE TARGETED APPLICATION OF REAGENTS ONTO IMMOBILIZED BIOLOGICAL MATERIAL

RELATED APPLICATION

This application is a Continuation-in-part of U.S. application Ser. No. 09/432,671, filed on Nov. 2, 1999, now abondoned and is incorporated herein by reference.

FIELD OF THE INVENTION

The present invention is relative to a method for the purposeful application of at least one reagent onto immobilized biological material as well as to a diagnostic kit containing small surface templates on which at least one reagent is fixed for contact hybridization.

BACKGROUND OF THE INVENTION

Modern methods for investigating immobilized biological material such as, e.g., cells or chromosomes frequently use expensive reagents such as fluorochromes that are used for marking. Examples of such methods are, among others FISH (fluorescence in-situ hybridization) and multicolor FISH methods, in which the cells are hybridized, e.g., with fluorescence-marked nucleic-acid probes or probe mixtures. One example of the application of such FISH methods is metaphase analysis. Only a small portion of the reagent DNA probes are utilized in the analysis since the metaphase chromosomes form only a small part of the hybridized material. The vast majority of the DNA probes therefore remains unused and is washed off and discarded.

Accordingly there remains room for improvement and variation within the art.

SUMMARY OF THE INVENTION

One aspect of the present invention is to provide an improved method and apparatus for the selective addition of minute amounts of reagents onto specified areas of a substrate such as a microscope slide. The microscope slide contains a biological material of interest, such as metaphase chromosomes, which is fixed to the slide. Thereafter, controlled volumes and precise placement of reagents such as fluorescence marked DNA probes are added only to select portions of the microscope slide. In this manner, only the actual material of interest is treated with expensive reagents, thereby conserving reagents by precise application to a small portion of material fixed on a substrate.

Yet another aspect of the present invention is to provide a method for the targeted application of at least one reagent onto immobilized biological material which thereby improves utilization of the reagents to be applied.

Yet another aspect of the present invention is directed to the in-situ analysis of a rare cell population among a large number of cells on a slide. For example, in the assessment and characterization of disseminated tumor cells in bone marrow or peripheral blood the rate of the cells of interest may be as low as 1 to 5 tumor cells in a million of normal cells. In prenatal genetic analysis based on fetal cells circulating in the maternal bloodstream occurrence rates of fetal cells are even much lower. It is obvious that the greatest part of the DNA probes, therefore, remains unused and is washed off and discarded when the whole slide area containing immobilized biological material is hybridized.

These and other features, aspects, and advantages of the present invention are provided by a method and apparatus comprising a method for the targeted application of at least one reagent onto one or more small regions of interest containing a low occurrence of biological objects of interest within a large amount of immobilized biological material comprising the steps of (a) depositing immobilized biological material selected from the group consisting of tissue, cells, cell parts, and chromosomes onto a support slide; (b) placing the support slide having the immobilized biological material onto an automated optical scanning device; (c) automatically detecting objects of interest within the biological material and recording their positions with respect to the slide; (d) automatically positioning a micropipette over the regions of interest defined by the positions of the biological objects of interest recorded during step (c); and, applying the reagent onto the regions of interest.

An additional aspect of the invention can be provided by a method for the targeted application of at least one reagent onto one or several small regions of interest containing biological objects of interest within a large amount of immobilized biological material comprising the steps of (a) depositing immobilized biological material selected from the group consisting of tissue, cells, cell parts, and chromosomes onto a support slide; (b) placing the support slide having the immobilized biological material onto an automated optical scanning device; (c) automatically detecting the biological objects of interest and recording their positions on the slide; (d) automatically marking the positions recorded during step (c) by contacting the slide with a marking device; and, (e) manually applying the reagent onto the regions of interest centered around the positions that have been marked during step (d).

A dispensing apparatus useful for the present invention can be provided by a dispensing apparatus for the application of reagents in conjunction with an optical microscope comprising: (a) the housing defining a top, a bottom, and at least one sidewall, the top defining a threaded surface, the threaded surface adapted for securement to a turret of an optical microscope; (b) a first opening defined along the bottom of the housing, the opening in axial alignment with a central axis defined along a length of the housing; (c) a conduit, defined within an interior of the housing, the conduit in communication with the first opening and in further communication with a second opening defined along a sidewall of the housing; (d) wherein, when the first opening, the conduit, and the second opening are in communication with a micropipette dispenser, a controlled volume of a reagent may be delivered from the micropipette dispenser to a substrate opposite the first opening.

BRIEF DESCRIPTION OF THE DRAWINGS

A full and enabling disclosure of the present invention, including the best mode thereof, to one of ordinary skill in the art, is set forth more particularly in the remainder of the specification, including reference to the accompanying drawings.

DESCRIPTION OF THE PREFERRED EMBODIMENT

Figure 1:
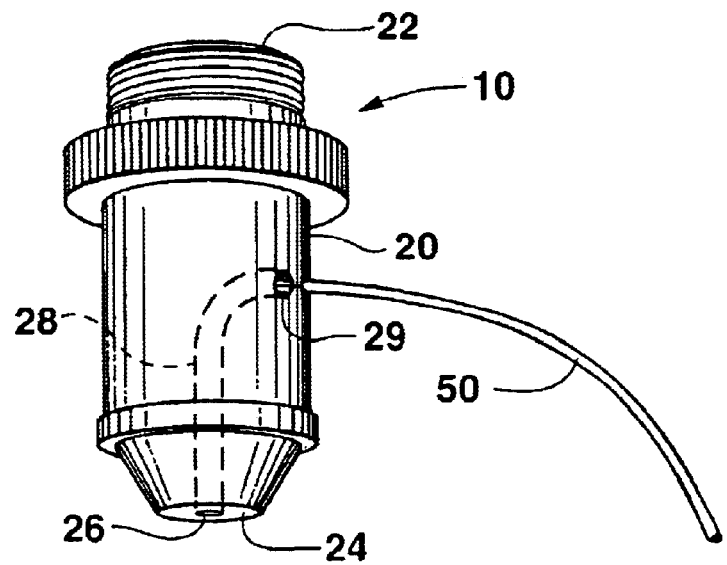
FIG. 1 sets forth a reagent dispensing apparatus which is adapted for attachment to the turret of a microscope.

Reference now will be made in detail to the embodiments of the invention, one or more examples of which are set forth below. Each example is provided by way of explanation of the invention, not limitation of the invention. In fact, it will be apparent to those skilled in the art that various modifications and variations can be made in the present invention without departing from the scope or spirit of the invention. For instance, features illustrated or described as part of one embodiment, can be used on another embodiment to yield a still further embodiment. Thus, it is intended that the present invention cover such modifications and variations as come within the scope of the appended claims and their equivalents. Other objects, features, and aspects of the present invention are disclosed in the following detailed description. It is to be understood by one of ordinary skill in the art that the present discussion is a description of exemplary embodiments only and is not intended as limiting the broader aspects of the present invention, which broader aspects are embodied in the exemplary constructions.

In describing the various figures herein, the same reference numbers are used throughout to describe the same material, apparatus or process pathway. To avoid redundancy, detailed descriptions of much of the apparatus once described in relation to a figure is not repeated in the descriptions of subsequent figures, although such apparatus or process is labeled with the same reference numbers.

The term "biological material" as used herein includes cells, cell fractions, cellular organelles, cell tissues, and cellular components such as chromosomes. For purposes of the present description and examples, special reference will be made to the biological material of metaphase chromosomes. However, one having ordinary skill in the art will recognize that this non-limiting example is for the purposes of illustration only and that other biological materials as defined above may be readily adapted to the present methodology.

The term "carrier" includes all objects on which the biological material can be held, especially microscope slides.

The term "immobilized" signifies that the biological material is anchored and/or fixed on the carrier with the aid of methods known to the art.

The term "objects of interest" refers to a subset of relevant cells or other portions of the biological material which are to be treated in a targeted manner so as to minimize the volume of reagent used in the investigative protocol. For instance the objects of interest, such as, e.g., cells or chromosomes, can be marked with one or several specific markers, e.g., surface markers such as marked antibodies or, e.g., 23 different, distinguishably marked probes for human chromosome analysis.

Further, the expression "objects of interest" can comprise a sub-population of the "biological material" e.g., cells or cellular components such as chromosomes. Objects of interest can be rare disseminated tumor cells in bone marrow or peripheral blood, or rare cells of fetal origin circulating in the bloodstream of a pregnant woman. Objects of interest can be labeled with one or several specific markers, e.g., surface markers such as labeled antibodies, cytoplasmic markers such as labeled RNA to distinguish the objects of interest from all the other objects within the biological material. If the objects of interest can be distinguished by their shape, the complete biological material can be stained with an unspecific stain, e.g., a DNA stain like Giemsa or DAPI, and the identification of the objects of interest can be done by analyzing the morphology. The expression "automated optical scanning device" can comprise an automated microscope combined with digital image analysis. The microscope (e.g., Carl Zeiss Axioplan2 Imaging Mot) is equipped with a motorized focus and a motorized objective lens revolver. A motorized x-y scanning stage (available from Maerzhaeuser, Wetzlar Germany) accommodates 8 slides. A CCD camera (e.g., available from JAI, Denmark) is attached to the microscope to capture images that are analyzed by a personal computer. The personal computer controls the motorized stage and scans the slide while keeping the slide in the plane of focus. Each field of view is captured and analyzed; the objects of interest are identified by appropriate classification algorithms while their coordinates are recorded and an image gallery of identified objects of interest is being built up. After the scan of a single or multiple slides, any of the found objects can be automatically relocated by a mouse click on the respective gallery image. This will move the motorized x-y stage to the prior coordinate of the selected object of interest and may then be visually inspected through the microscope if desired. Such a scanning system is commercially available and is being used for automatic metaphase finding as set forth in the publications by J. Weber, W, Scheid, and H. Traut, "Time-saving in Biological Dosimetry by Using the Automatic Metaphase Finder Metafer 2," *Mutation Research*, 272 (1992), pp. 31–34, and R. Huber, U. Kulka, T. Lörch, H. Braselmann, and M. Bauchinger, "Automated Metaphase Finding: An Assessment of the Efficiency of the Metafer 2 System in Routine Mutagenicity Assay", *Mutation Research*, 334 (1995), pp 97–102. The automatic detection of rare cells is reported in G. Méhes, T. Lörch, and P. F. Ambros, "Quantitative Analysis of Disseminated Tumor Cells in the Bone Marrow by Automated Fluorescence Image Analysis," *Cytometry*, 42 (2000), pp 357–362, and in the publication by G. Méhes, A Luegmayr, C. M. Hattinger, T. Lörch, I. M. Ambros, H. Gadner, and P. F. Ambros, "Automatic Detection and Genetic Profiling of Disseminated Neuroblastoma Cells," *Medical and Pediatric Oncology*, 36 (2001), pp. 205–209. The above four references are hereby incorporated by reference in their entirety.

Figure 3:
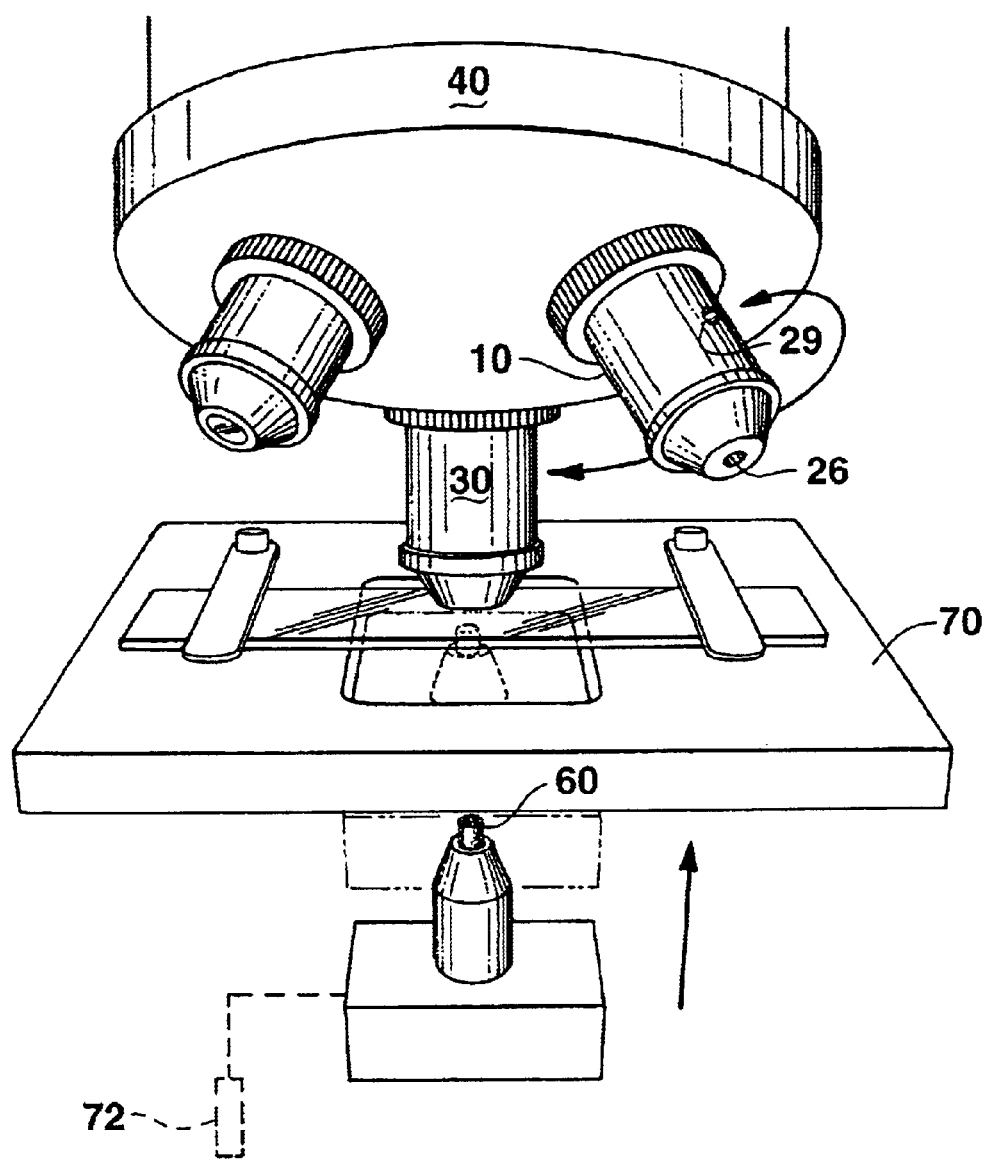
FIG. 3 is a schematic view illustrating a marking device and process for placing an indicia along a bottom of a microscope slide to indicate a field of interest which may thereafter be returned to for further visualization and study.

The visualization of the immobilized biological material to be investigated in step (a) of the method of the invention can take place using a scanning device or a device for directed scanning such as, e.g., an optical microscope. As best seen in reference to FIGS. 1 and 3, in a preferred embodiment of the invention the microscope objective lens is replaced by a dispensing apparatus 10 adapted for applying at least one reagent. According to a preferred embodiment of the method of the invention, one or several photographs of the immobilized biological material found can be recorded during step (a) in combination with a scanning device and an image processing unit, e.g., a CCD [charge-coupled device] camera. The photographs can preferably be displayed together for the pre-selection of suitable immobilized biological material. The recording of the position of the immobilized biological material can take place, e.g., with the aid of a device for scanning the position, e.g., of the slide stage of a microscope in combination with a computer-supported recording/processing and storage of the positional data of the immobilized biological material on preferably digital storage media such as diskettes, hard disks, removable disk units, optical storage media such as compact disks, etc.

Thereafter, at least one reagent can be applied to the one or more locations of objects of interest contained on the microscope slide. One apparatus useful for applying reagents to the microscope slide includes the microvolume dispensing apparatus 10 as set forth in FIGS. 1 and 3. As best seen in reference to FIG. 1, the dispensing apparatus 10 defines a housing 20 having a threaded top portion 22 and a bottom portion 24. As seen in reference to the figures, the dispensing apparatus 10 has a size, shape, and physical appearance similar to that of a standard objective microscope lens 30. The threaded portion 22 is adapted for installation onto a standard threaded objective receptacle carried on a turret 40 of a conventional light microscope. Along an axial center of the dispensing apparatus 10, an outlet 26 is defined along bottom surface 24. Outlet 26 is in further communication with a conduit 28 defined within an interior of the dispensing apparatus 10. Housing 20 defines a second opening 29 which may be along a sidewall of housing 20. The conduit 28 is adapted for receiving therethrough a length of a microdispensing tube 50. Preferably, the inserted end of micro tube 50 is designed to interengage with the opening 26 so that micro tube 50 does not extend beyond the confines of aperture 26. As alternatively stated, in Applicant's preferred embodiment the micro tubing 50 should not extend beyond the plane of bottom surface 24.

While not separately seen, the free end of micro tubing 50 may be attached to a conventional micropipette dispenser through which a known microvolume of a fluid may be dispensed either manually or through an automated system.

The dispensing apparatus 10 does not require any optical system. As such, the housing can be constructed of a variety of materials which may include metals or plastic which may either be disposable or cleaned for re-use. The use of a micro tubing 50 in conjunction with the dispensing apparatus 10 greatly facilitates the interchangeability and cleaning of dispensing apparatus 10 between uses or when going from one reagent to a second reagent.

As is readily appreciated by one having ordinary skill in the art, various microscope objectives have differing magnifications and therefore have different fields of view. Further, effective working distances between the objectives and the adjacent microscope slide also differ. Accordingly, it is preferred to provide a dispensing apparatus 10 which is adapted for a particular microscope objective's field of view and will be approximately spaced at a useful dispensing distance from the microscope slide.

Figure 2:
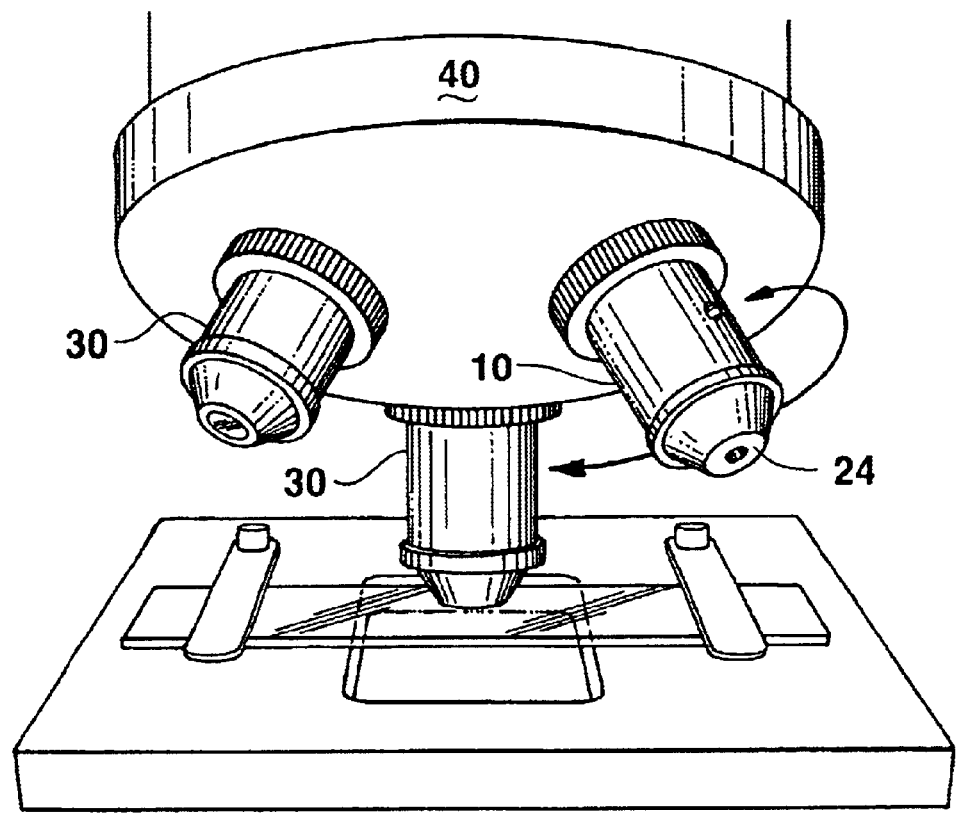
FIG. 2 is a schematic view illustrating the change of the objective lens to the dispensing apparatus by rotation of the microscope turret.

As best seen in reference to FIG. 2, it is preferred that as an objective 30 is rotated about the microscope turret 40, the dispensing apparatus 10 will automatically be positioned opposite the microscope slide so that apparatus 10 is of a proper height and has a proper dispensing orifice and volume capabilities to direct a reagent onto the field of view of the prior objective lens 30. In this respect, an objective lens having a greater magnification uses a dispensing apparatus 10 adapted for providing a smaller volume of reagents and/or application of the reagent to a more localized area of the microscope slide.

As illustrated in FIG. 1, it is preferred that the orifice 26 in communication with the micropipette dispenser, be in a precise axial alignment with the prior objective's field of view. In this manner, the prior field of view of the objective lens 30 will be the portion of the microscope slide in which the reagent is dispensed through orifice 26. The rotation of the turret to the dispensing position may be controlled by the software used to identify and locate the objects of interest.

According to a preferred embodiment of the method of the present invention the application of the at least one reagent and/or the application of the small-area, local cover take(s) place automatically. In a further, preferred embodiment of the method of the invention small cover slips may be used to cover the treated object of interest during the reagent incubation step.

According to a preferred embodiment of the present invention at least one intermediate step for treating, preferably washing the immobilized biological material can be intercalated between the finding of the immobilized biological material to be investigated while recording its position in step (a) and between the positioning of a device for applying the at least one reagent over the position, recorded in step (a), of the immobilized biological material in step (b).

According to a second embodiment of the invention a micropipette is positioned at a fixed point within the range of movement of the motorized stage. In this embodiment, the object of interest on the slide can be positioned under the micropipette. By the prior marking of the slide either by a physical mark as described below or in combination with the motorized stage, the object of interest on the slide may be positioned underneath the micropipette where the desired volume of reagent may be dispensed.

According to a preferred embodiment of the method of the invention the objects of interest can be pre-selected from the image gallery by an operator to reject objects that have not been recognized correctly by the image analysis system (false positives) or that are for other reasons not suitable for analysis. During the automatic application or the reagents the system will skip the object positions of rejected objects.

According to a further embodiment of the method of the invention it is preferred that an evaluation is carried out after step (c) or (d) by positioning an analyzing device comprising, e.g., a scanning device or a device for directed scanning comprising, e.g., a device for photometric and/or chemiluminometric, such as fluorometric measurements, above the position, recorded in step (a), of the immobilized biological material.

In an alternative embodiment of the method according to the present invention the positions of the objects of interest are marked using a marking device for subsequent manual application of a small amount of reagent to this area. As seen in reference to FIG. 3, a preferred embodiment of the method of the invention the marking device 60 is a pen or a diamond tip attached to the condenser mount underneath the slide. By lowering the microscope stage 70 the computer 72 can bring the backside of the slide in mechanical contact with the marking device 60 in order to put a mark at the position of the currently relocated object of interest. After removing the slide from the scanning system, manual application of a small amount of reagent can be performed in the conventional way. As the preferred labeling methods use fluorescent dyes and epi-illumination, the mark on the backside of the slide will not interfere with the subsequent microscopic analysis. Further, the marking apparatus can be used in conjunction with the automated methodology set forth above. The physical marking of the slide will facilitate the location of objects of interest if the slide is later viewed on different equipment.

According to a further embodiment of the method of the invention the at least one reagent comprises a nucleic acid selected from DNA or RNA or comprises a polypeptide. The concept "nucleic acid" signifies native, semisynthetical or modified nucleic-acid molecules of desoxyribonucleotides and/or ribonucleotides and/or modified nucleotides such as aminonucleotides or ($\alpha$-S)-triphosphate nucleotides. A polypeptide can comprise, e.g., a protein such as an antibody which can be polyclonal or monoclonal.

According to a further embodiment of the method of the invention the at least one reagent is provided with one or several marker molecules. The concept of a "marker" signifies suitable, directly or indirectly detectable atoms or molecules which are inserted into the molecules of the at least one reagent or are connected with them. Suitable markers are, e.g., those comprising radioactive isotopes inserted onto nucleotides or onto polypeptides, e.g., antibodies, coupled fluorescent dyes and/or biotin and/or digoxigenin and/or into nucleotides or into polypeptides, e.g., antibodies. In a preferred embodiment the marker includes a fluorescent dye with sufficient affinity and specificity for immunofluorescence microscopy. The selection of appropriate substrates, and the fluorescent behavior of the emission spectra such as, e.g., cumarins and rhodamines and/or fluorescent isothiocyanates and europium-chelate-marked and porphyrin[e]-marked avidins are well known within the art.

According to a further preferred embodiment of the method of the invention the at least one reagent is capable of hybridization or an antigen/antibody reaction or a ligand/protein reaction. The concept "hybridization", especially "in-situ hybridization" signifies the binding of a synthetically produced DNA/RNA probe provided with biological, physical or chemical markings for detection as reagent molecule to native, naturally occurring DNA/RNA sequences. The binding is achieved by a conventional denaturing and renaturing of the corresponding nucleic acids. Of course, these DNA/RNA probes contain at least one sequence section capable of hybridizing onto a DNA/RNA sequence of the molecules of the immobilized biological material such as a chromosome. This sequence section comprises a specific, individual sequence range, preferably 100 to 1,000 base-pairs long, of the reagent molecule which is added to a complementary range of the molecule of the immobilized biological material at a suitable temperature, preferably 60° C. or less, and at a suitable saline concentration which preferably contains 50 to 300 mmol/l of monovalent ions and 0 to 10 mmol/l of bivalent ions under formation of hydrogen bridges.

Further subject matter of the present invention is constituted by a diagnostic kit for investigating immobilized biological material according to one of the previously defined methods. For instance, cover slips may be used in which the biological material and accompanying objects of interest are fixed and visualized through light microscopy. Thereafter, the reagents may be applied according to the apparatuses and methodologies set forth above. The use of small cover slips combined with the small volumes of needed reagents enables economical commercial kits to be prepared for rapid analysis using contact hybridization, antibody screenings, or other similar diagnostic and evaluative techniques. In addition, small volumes of reagent may be applied through capillary action between the slide and the adjacent cover slip, again minimizing the volume of needed reagent.

In the instance of metaphase analysis the method of the invention is carried out in such a manner that a device for the purposeful relocalization of objects of interest of suitable metaphase chromosomes is provided. The methodology is rapid, reliable, and lends itself to automation. The positions of manually or automatically located metaphase chromosomes are stored. The found metaphase chromosomes are subsequently automatically positioned under a dispensing apparatus, such as a pipette having the probe solution. The hybridization probe solution is applied in a small amount to a directed target. In a further step the found metaphase chromosomes can be positioned under a further pipette or suitable dispenser in order to automatically apply a small cover glass.

The consumption of material, e.g., in hybridizations of metaphase chromosomes with DNA probes can be reduced by a factor of 10 or more with the aid of the method of the invention and the aid of the kit in accordance with the invention. This is especially significant in tumor cytogenetics, where the number of metaphases per microscope slide is low. The invention provides for the pre-selection of metaphases, e.g., in accordance with an embodiment of the present invention, via a display of the photographs of the automatically found metaphases, exhibiting a chromosome quality suitable for the evaluation, before the application of the DNA probes is of interest.

The method of the invention and the diagnostic kit of the invention can be equally used on interphase cells previously marked with suitable markers, exhibiting certain properties and occurring with low frequency in the preparation such as, e.g., tumor cells during the detection of minimal residual disease or [on] fetal cells in the mother's blood.

Although preferred embodiments of the invention have been described using specific terms, devices, and methods, such description is for illustrative purposes only. The words used are words of description rather than of limitation. It is to be understood that changes and variations may be made by those of ordinary skill in the art without departing from the spirit or the scope of the present invention, which is set forth in the following claims. In addition, it should be understood that aspects of the various embodiments may be interchanged, both in whole or in part. Therefore, the spirit and scope of the appended claims should not be limited to the description of the preferred versions contained therein.

That which is claimed:

1. A method for the targeted application of at least one reagent onto immobilized biological material comprising the steps of:
   (a) localizing immobilized biological material selected from the group consisting of cells, cell parts, and chromosomes onto a support slide;
   (b) placing the support slide having the immobilized biological material onto an optical scanning device comprising an automated microscope having a camera combined with a digital image analyzer;
   (c) analyzing electronically images captured by the camera and identifying the an object of interest of the immobilized biological material;
   (d) recording electronically the position of the objects of interest of the immobilized biological material with respect to the automated optical scanning device;
   (e) automatically positioning a micropipette over the position of the object of interest recorded in step (d); and,
   (f) applying a reagent onto the object of interest.

2. The method according to claim 1 wherein a lens position on a turret of the microscope is occupied with a micropipette.

3. The method according to claim 1 wherein the applying step further comprises applying the reagent in a localized area substantially limited to the position of the object of interest.

4. The method according to claim 1 wherein the step of applying the reagent further includes the use of an automated pipette for dispensing a pre-selected volume of the reagent.

5. The method according to claim 3 wherein the step of applying the reagent onto a localized area further includes placing a cover slip over the immobilized biological material following the step of applying a reagent.

6. The method according to claim 1 further comprising the additional step of photographing the immobilized biological material.

7. The method according to claim 6 wherein the photographs are displayed, thereby providing an additional selection step for selecting only positions corresponding to a selected displayed photograph for the applying step.

8. The method according to claim 1 comprising the additional step of washing the immobilized biological material following an incubation interval.

9. The method according to claim 1 comprising the additional step of washing the reagent applied to the object of interest following application of the reagent.

10. The method according to claim 9 comprising the additional step of positioning an analyzing device over the recorded position of the object of interest.

11. The method according to claim 1 wherein the object of interest is labeled with a specific marker.

12. The method according to claim 1 wherein the immobilized biological material further comprises metaphase chromosomes.

13. The method according to claim 10 wherein the reagent is selected from a group consisting of a DNA, an RNA, and a polypeptide.

14. The method according to claim 1 wherein the reagent further comprises a plurality of different labelings.

15. The method according to claim 14 wherein at least one of said plurality of reagents further comprises a fluorescent dye.

16. The method according to claim 13 wherein the reagent specifically binds to the object of interest.

17. The method according to claim 16 wherein the specific binding of the reagent to the object of interest is a hybridization reaction.

18. The method according to claim 1 wherein said step (d)recording electronically the position of an object of interest further includes recording a plurality of objects of interest positioned on a single support slide and thereafter sequentially automatically positioning a micropipette and applying a reagent corresponding to the recorded position of each of said plurality of objects of interest.

19. A method for the targeted application of at least one reagent onto one or several small regions of interest containing biological objects of interest within a larger region of immobilized biological material comprising the steps of:
 (a) providing a biological material selected from the group consisting of tissue, cells, cell parts, and chromosomes, said biological material immobilized onto a support slide;
 (b) placing the support slide having the immobilized biological material onto an automated optical scanning device comprising an automated microscope having a camera combined with a digital image analyzer;
 (c) automatically detecting at least one biological object of interest of said biological material immobalized onto a support slide by analyzing electronically images captured by the camera and identifying the objects of interest;
 (d) recording electronically the position of the at least one biological object of interest of the immobilized biological material with respect to the slide;
 (e) automatically positioning a micropipette over the position of said at least one biological object of interest recorded during step (c); and
 (f) applying a reagent onto the at least one biological object of interest.

20. The method according to claim 19 wherein the optical scanning device is a microscope comprising a motorized x-y stage and motorized focus control which is connected to a digital image analysis system.

21. The method according to claim 20 wherein a micropipette device is attached to an empty objective position of the objective turret of the microscope and wherein the micropipette is brought into the optical axis of the microscope by switching the objective turret between the observation position and the pipette position.

22. The method according to claim 21 wherein the step of applying the reagent further includes the use of an automated pipette for dispensing a pre-selected volume of the reagent.

23. The method according to claim 19 wherein the step of applying the reagent onto said at least one biological object of interest further includes placing a cover slip over the region of interest following the step of applying the reagent.

24. The method according to claim 19 further comprising the additional step of automatically relocating the said at least one biological object of interest to the position recorded in step (c) following said step (d).

25. The method according to claim 19 further comprising the additional step of automatically recording an image of the at least one biological object of interest.

26. The method according to claim 25 further comprising the additional step of reviewing a gallery of recorded images on a display device for selecting from a plurality of biological objects of interest suited for applying the reagent.

27. The method according to claim 19 wherein the at least one biological material of interest is labeled with a specific marker.

28. The claim according to claim 27 wherein the specific marker is detected by means of a chromogenic or fluorescent dye.

29. The method according to claim 19 wherein said step (d) recording electronically the position of an object of interest further includes recording a plurality of objects of interest positioned on a single support slide and thereafter sequentially automatically positioning a micropipette and applying a reagent corresponding to the recorded position of each of said plurality of objects of interest.

30. A method for the targeted application of at least one reagent onto immobilized biological material comprising the steps of:
 (a) localizing immobilized biological material selected from the group consisting of cells, cell parts, and chromosomes onto a support slide;
 (b) placing the support slide having the immobilized biological material onto an optical scanning device comprising a microscope having a camera combined with a digital image analyzer;
 (c) recording electronically the position of an object of interest of the immobilized biological material with respect to the optical scanning device;
 (d) automatically positioning a micropipette over the position of the object of interest recorded in step (c), the micropipette is located within a turret of said microscope; and,
 (e) applying the reagent onto the object of interest.

31. The method according to claim 30 wherein the microscope is an automated microscope.

32. The method according to claim 31 comprising the additional step of analyzing electronically images captured by the camera and identifying the objects of interest.

33. The method according to claim 31 comprising the additional step of positioning an analyzing device over the recorded position of the object of interest.

34. The method according to claim 30 wherein said step (d) further comprises placing a micropipette into the optical axis of the microscope by switching the objective turret between an observation position and a pipette position, and the pipette being positioned within an empty objective position of the turret of the microscope.

* * * * *